(12) United States Patent
Haid et al.

(10) Patent No.: US 7,300,441 B2
(45) Date of Patent: Nov. 27, 2007

(54) TECHNIQUE AND INSTRUMENTATION FOR PREPARATION OF VERTEBRAL MEMBERS

(75) Inventors: Regis W. Haid, Atlanta, GA (US); Vincent C. Traynelis, Iowa City, IA (US); Thomas A. Zdeblick, Middleton, WI (US); Bradley J. Coates, Rossville, TN (US); Greg C. Marik, Germantown, TN (US); Craig M. Squires, Memphis, TN (US); Courtney S. Williams, Memphis, TN (US); Linda M. Holmes, Bartlett, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 539 days.

(21) Appl. No.: 10/644,681

(22) Filed: Aug. 20, 2003

(65) Prior Publication Data

US 2005/0043740 A1 Feb. 24, 2005

(51) Int. Cl.
*A61B 17/58* (2006.01)
*A61F 2/00* (2006.01)

(52) U.S. Cl. ...................................... 606/90
(58) Field of Classification Search ................ 606/53, 606/86, 87, 90, 99, 102, 105; 623/17.11–17.16
See application file for complete search history.

(56) References Cited

U.S. PATENT DOCUMENTS

| 5,489,307 | A | * | 2/1996 | Kuslich et al. ............. 128/898 |
| 6,080,155 | A | | 6/2000 | Michelson |
| 6,083,225 | A | * | 7/2000 | Winslow et al. ............... 606/61 |
| 6,096,038 | A | * | 8/2000 | Michelson .................... 606/61 |
| 6,113,602 | A | * | 9/2000 | Sand ............................ 606/61 |
| 6,159,214 | A | * | 12/2000 | Michelson .................... 606/80 |
| 6,270,498 | B1 | * | 8/2001 | Michelson .................... 606/61 |
| 6,440,139 | B2 | | 8/2002 | Michelson |
| 6,616,671 | B2 | * | 9/2003 | Landry et al. ................ 606/99 |
| 6,648,895 | B2 | * | 11/2003 | Burkus et al. ................ 606/90 |
| 6,743,234 | B2 | * | 6/2004 | Burkus et al. ................ 606/90 |
| 6,929,647 | B2 | * | 8/2005 | Cohen .......................... 606/99 |
| 7,033,362 | B2 | * | 4/2006 | McGahan et al. ............ 606/96 |
| 7,083,625 | B2 | * | 8/2006 | Berry .......................... 606/96 |
| 2001/0000532 | A1 | | 4/2001 | Michelson |
| 2003/0032962 | A1 | | 2/2003 | McGahan et al. |

FOREIGN PATENT DOCUMENTS

| WO | WO 01/62166 | 8/2001 |
| WO | WO 2004/000139 | 12/2003 |

* cited by examiner

*Primary Examiner*—Anuradha Ramana
(74) *Attorney, Agent, or Firm*—Coats & Bennett, P.L.L.C.

(57) ABSTRACT

Instrumentation and techniques for preparing vertebral members for insertion of an implant. Foundation instruments provide a reference relative to the vertebral members. The foundation devices guide the placement of one or more instruments that prepare the vertebral members. The instruments operatively align with the foundation instruments in a specific orientation to ensure proper placement relative to the vertebral members. Preparatory instruments may be used to further remove bone from the vertebral members. The preparatory instruments may be used prior to or after the other instruments. An insert is inserted and mounted to the vertebral members after the bone has been removed. A holder may be used for holding and placing the implant relative to the vertebral members.

10 Claims, 22 Drawing Sheets

TECHNIQUE AND INSTRUMENTATION FOR PREPARATION OF VERTEBRAL MEMBERS

BACKGROUND

Current surgical procedures often require a great deal of skill from the surgeon. The procedures may include making fine manipulations by hand using high-speed equipment. One example includes preparing opposing surfaces of vertebral members for receiving an intermediate device, such as preparing the end plates of adjacent vertebrae to receive a graft or interbody fusion device. Each of the end plates is contoured and shaped using a cutting instrument that is held and manipulated by the surgeon. The surgeon guides the cutting instrument by hand and relies upon experience and training to ensure the end plates are contoured correctly.

It may be difficult for the surgeon to determine the amount of contouring and shaping required for each of the vertebral members. A trial-and-error routine is performed as the surgeon removes a first amount of material from one or both surfaces and determines whether the spacing is adequate for receiving the intermediate device. If the spacing is not adequate, the surgeon removes an additional amount from one or both of the surfaces. This routine continues until the proper amount has been removed and the surfaces are adequately prepared. The surgeon is careful not to remove too much from either surface, and instead tends to remove small increments.

SUMMARY

The present invention is directed to devices and method of preparing vertebral members and for mounting an implant. The invention includes one or more foundation devices that are aligned relative to the vertebral members. The foundation device forms a reference relative to the vertebral members which are used for subsequent bone removal steps. A physician aligns one or more instruments relative to the reference and removes bone from the vertebral members. The alignment of the instruments with the reference ensures the proper amount and location of bone is removed. Preparatory instruments may be used to further remove bone from the vertebral members. The preparatory instruments may be used prior to or after the other instruments. An insert is inserted and mounted to the vertebral members after the bone has been removed. A holder may be used for holding and placing the implant relative to the vertebral members.

DETAILED DESCRIPTION

Figure 1:
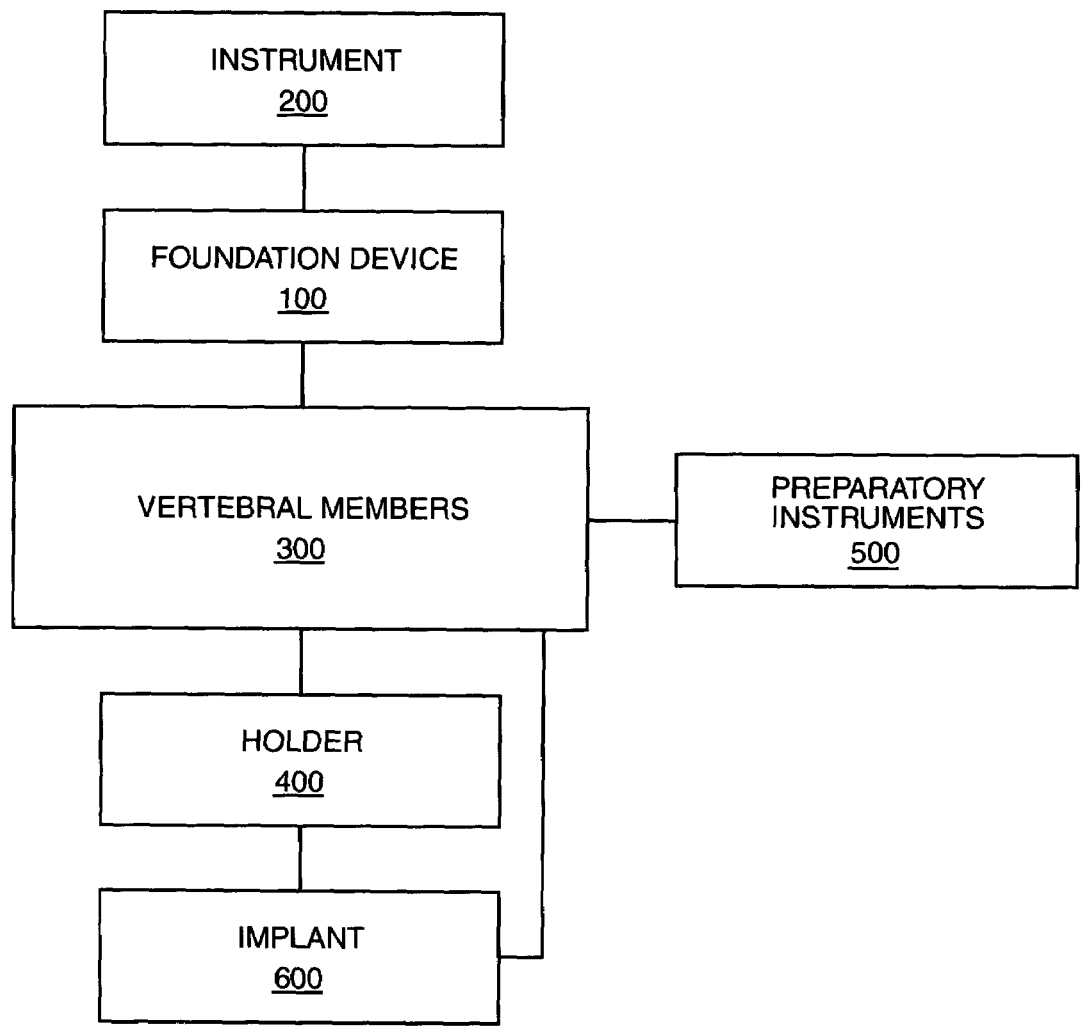
FIG. 1 is a schematic illustration of one embodiment of the components of the present invention for preparing the vertebral members for receiving an implant.

FIG. 1 illustrates a schematic representation of one embodiment of the present invention. Foundation device 100 is placed relative to the vertebral members 300 and is used as a reference for instruments 200. In one embodiment, foundation device 100 is attached directly to one or more vertebral members 300. In one embodiment, foundation device 100 is external to and does not contact the vertebral members. Foundation device 100 may include a single device, or may include multiple devices that are operatively connected. One or more instruments 200 prepare the vertebral members 300 for receiving the implant 600. Instrument 200 interacts with the foundation device 100 to ensure precise preparation of the vertebral members 300. Implant 600 is placed relative to the vertebral members 400. In one embodiment, implant 600 is placed via a holder 400. In another embodiment, implant 600 is placed directly to the vertebral members 300 without use of a holder 400. Preparatory instruments 500 further prepare the vertebral members 300 for receipt of the implant 600. In one embodiment, preparatory instruments 500 are applied directly to the vertebral members 300 without using the foundation device 100. Preparatory instruments 500 may be used at any stage of the process.

Figure 2:
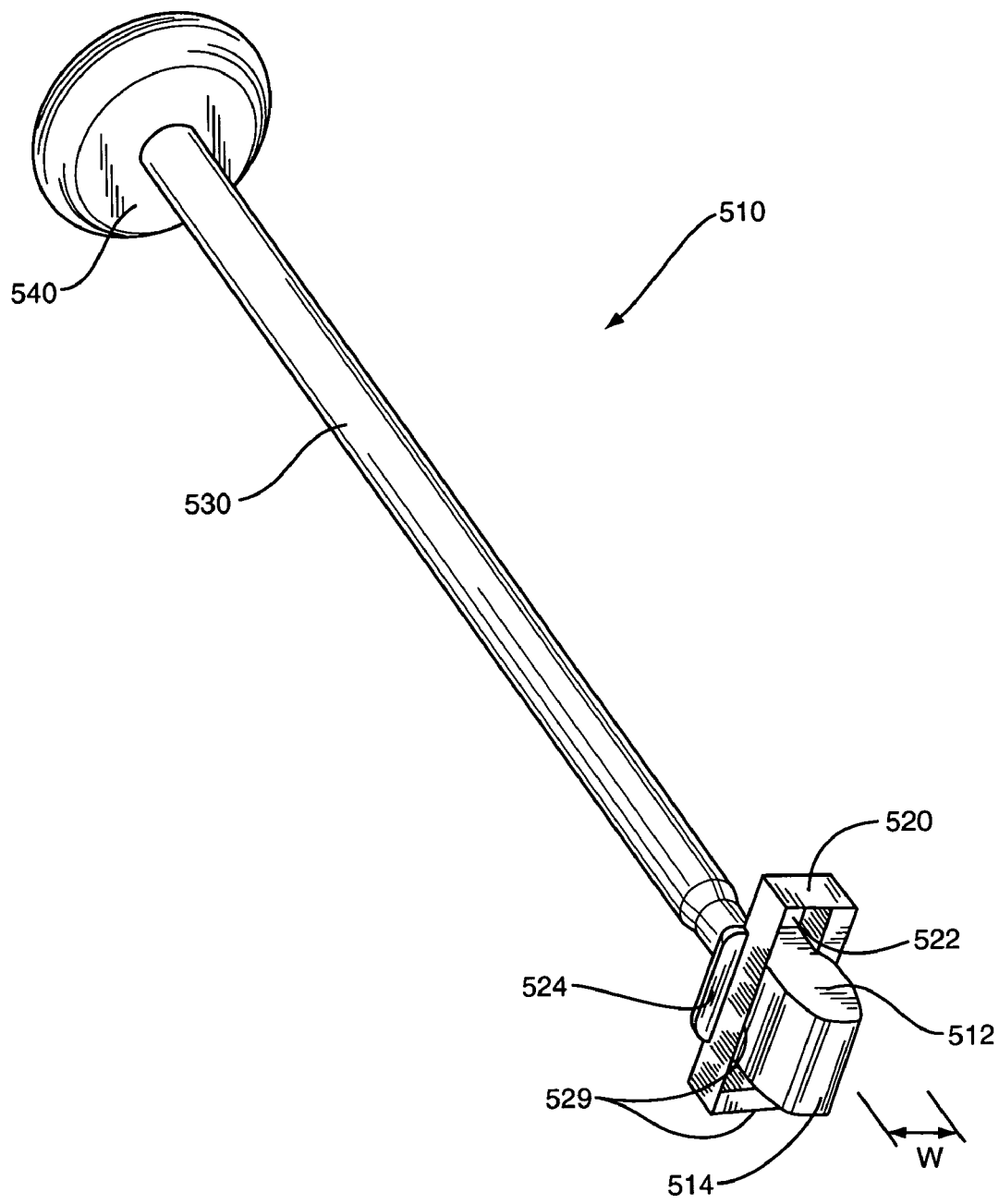
FIG. 2 is a perspective view of one embodiment of a template trial constructed according to the present invention.
Figure 3:
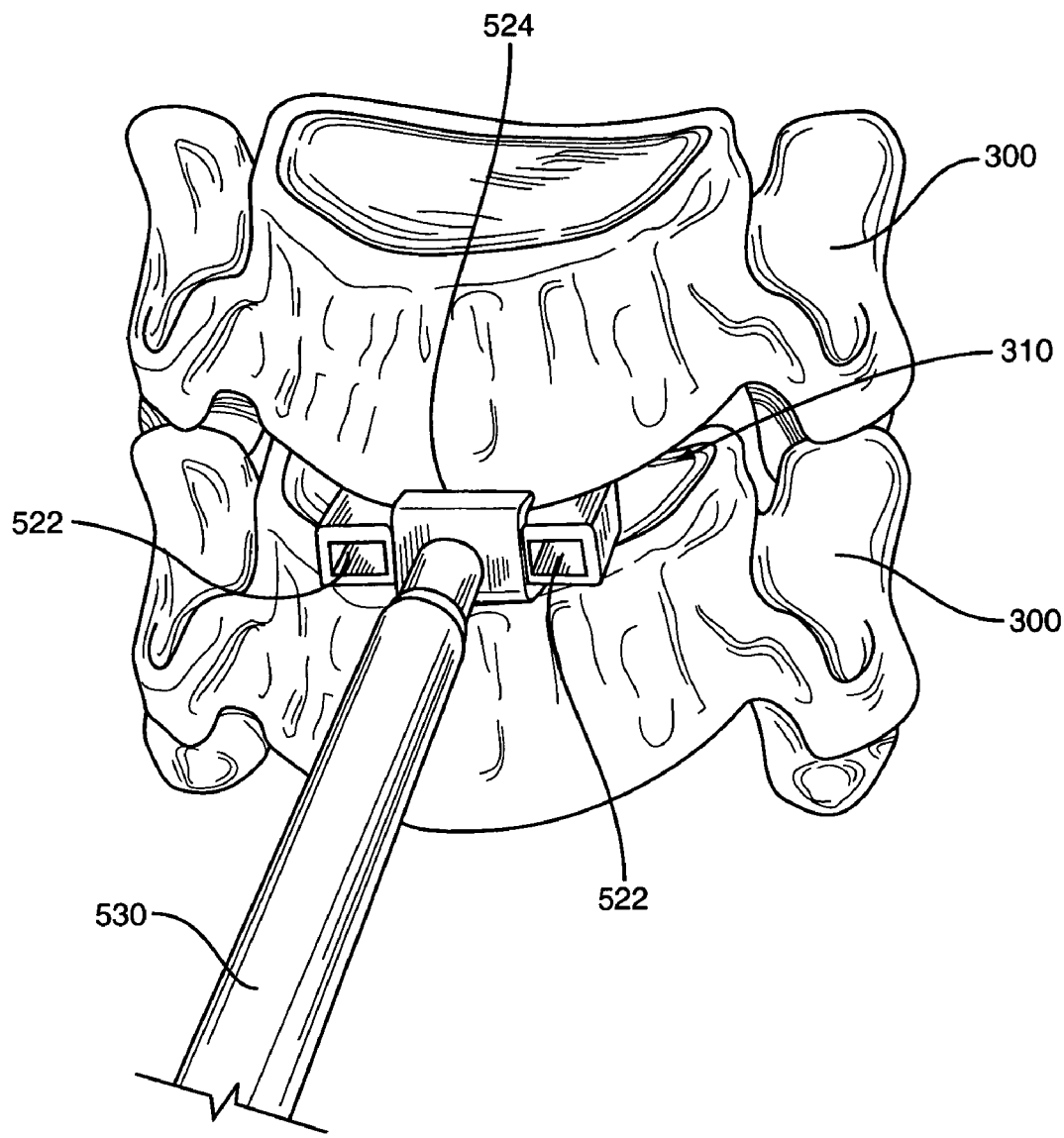
FIG. 3 is a partial perspective view illustrating one embodiment of the template trial positioned between adjacent vertebral members.

One preparatory instrument 500 is a template trial 510. One embodiment is illustrated in FIG. 2 and comprises a sizer 512 having a width w to be inserted within the disc space 310 between the adjacent vertebral members 300. Sizer 512 includes an angled tip 514 to ease the insertion between the vertebral members 300. As illustrated in FIG. 3, a first surface of the sizer 510 contacts a first vertebral member 300 and a second surface contacts the second vertebral member 300. Member 520 is attached to a proximal end of the sizer 512. In one embodiment, member 520 extends beyond the length of the sizer 512 forming windows 522 positioned along each lateral side. Windows 522 allow the physician to visibly see the lateral placement of the sizer 512 relative to the vertebral members 300. Depth stop protrusions 524 extend along opposing sides of the member 520. In one embodiment, depth stop protrusions 524 have a substantially linear edge. Each depth stop protrusion 524 may extend the entire length of the member 520, or a portion thereof. A rod 530 extends from the sizer 512. A head 540 is positioned at a proximal end of the rod 530. In one embodiment, head 540 provides an impact surface for applying a force to the template trial 510.

Figure 4:
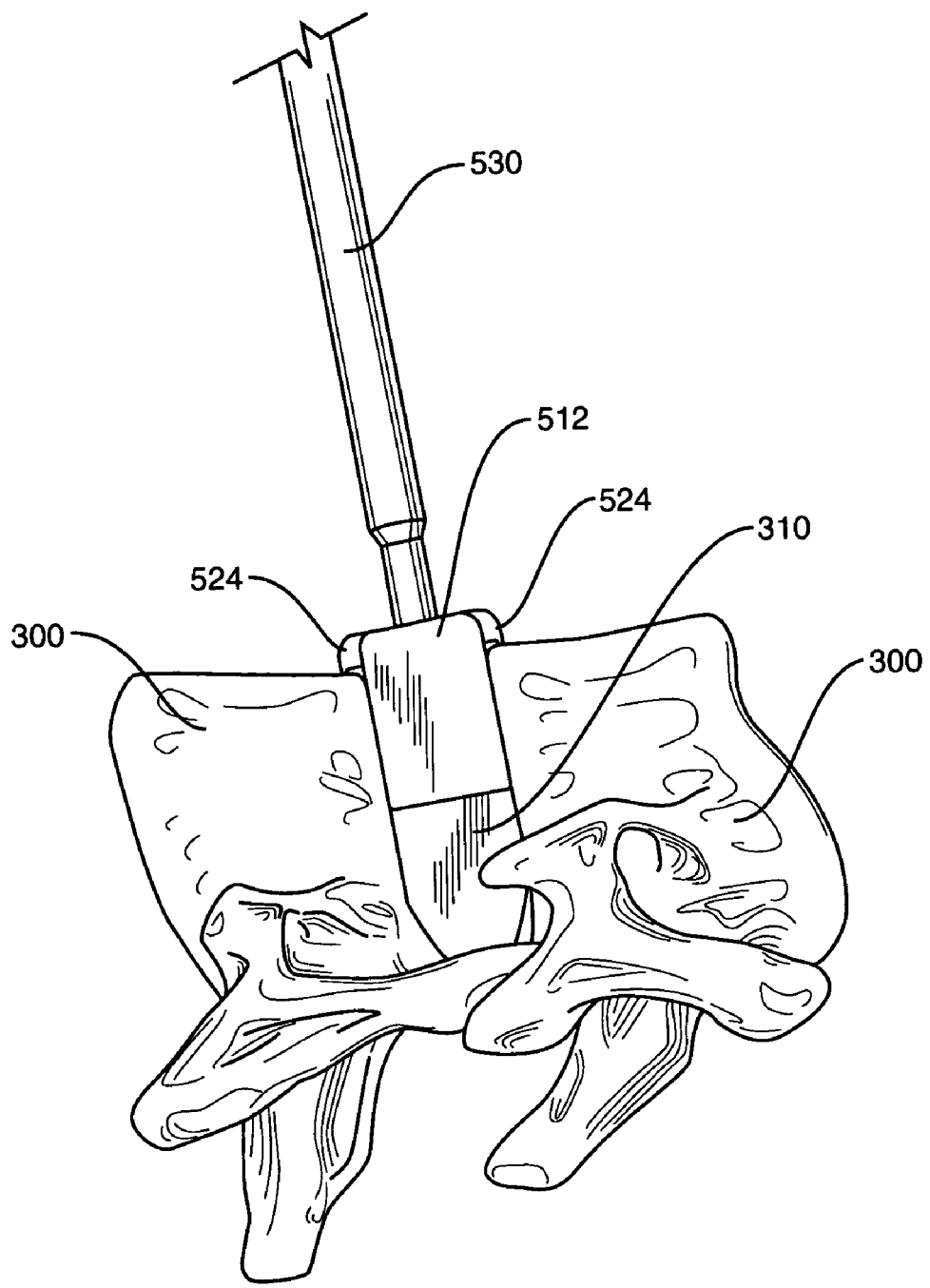
FIG. 4 is a side view of the embodiment of FIG. 3 illustrating the template trial positioned between adjacent vertebral members.

FIGS. 3 and 4 illustrate the template trial 510 positioned between the vertebral members 300 with the windows 522 used for lateral alignment. The template trial 510 is inserted to a point where the depth stop protrusions 524 engage the surface of the vertebral members 300. In one embodiment, one ore more cutting edges 529 on member 520 mark the verterbral members 300 indicating the amount of anterior bone that is to be removed to accommodate the foundation device 100 and/or implant 600. The template trial 510 is removed and the templated bone is removed both laterally and posteriorly. In one embodiment, a high-speed burr is used to remove the bone.

Figure 5:
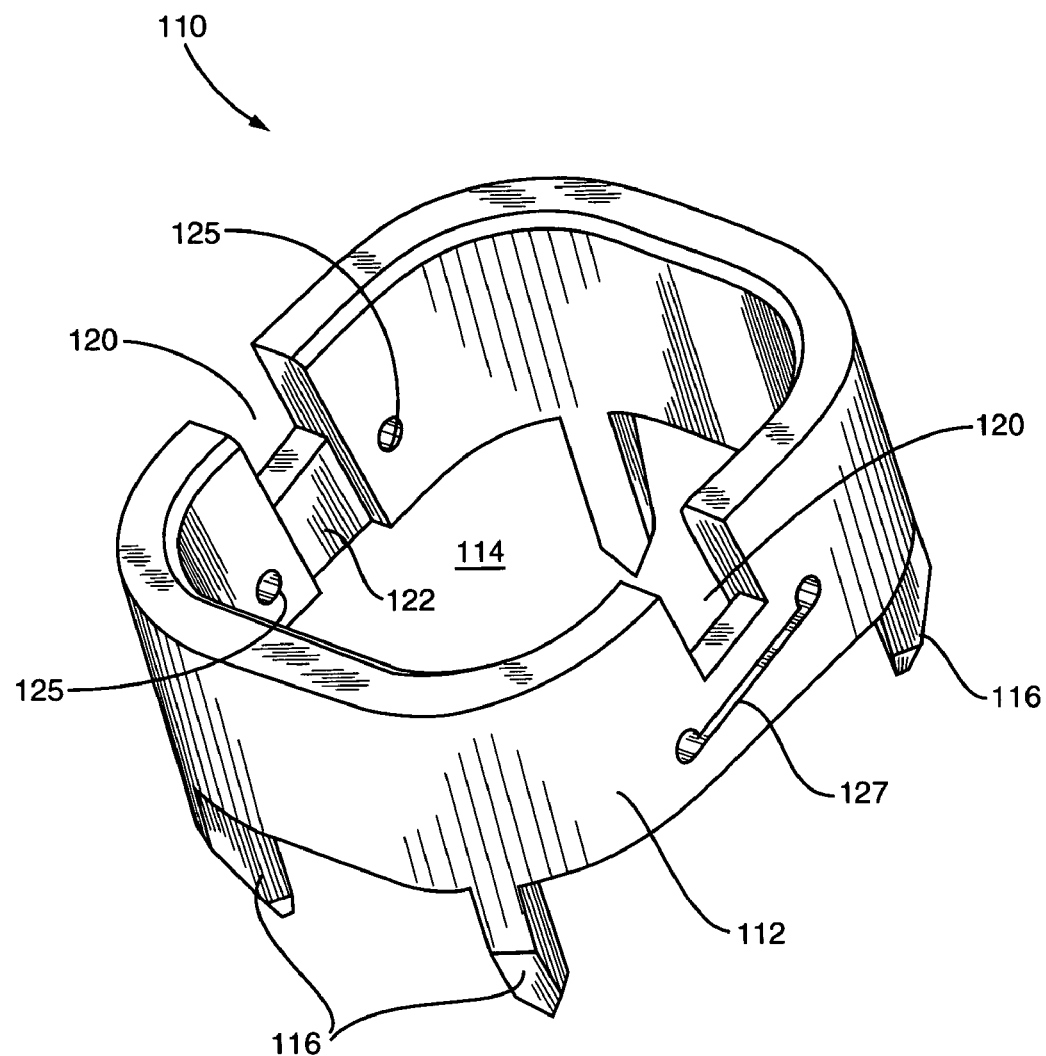
FIG. 5 is a perspective view of one embodiment of a docking ring constructed according to the present invention.

One or more foundation devices 100 align with the vertebral members 300 to provide a reference for instruments 200. One foundation device 100 includes a docking ring 110 as illustrated in FIG. 5. Docking ring 110 comprises a body 112 forming a window 114. In one embodiment, window 114 has a substantially rectangular shape. A plurality of spikes 116 extend outward from a distal side of the body 112 to mount the docking ring 110 relative to the vertebral members 300. In one embodiment, spikes 116 are ground with a point of the spike toward the median of the docking ring 110 with an angled portion on the outside. This configuration provides for the spikes 116 to engage the vertebral members 300 more readily during insertion than if the spikes 116 were ground from the opposite direction which could result in splaying of the spikes 116. In one embodiment, a total of four spikes 116 extend outward and the docking ring 110 is placed with two spikes 116 in the first vertebral member 300, two spikes 116 in the second vertebral member 300, and the window 114 positioned to extend over the endplates and disc space 310 of the vertebral members 300.

A pair of channels 120 are positioned on opposing sides of the docking ring 110. Channels open on the lateral side of the body 112 and extend a distance inward. Channels 120 may have varying widths and depths depending upon the application of use. In one embodiment, grooved sections 122 extend between a distal end of the channels 120 and the distal side of the body 112. In one embodiment, grooved sections 122 result in the body 112 having a narrower width at the channels 120. In one embodiment, grooved sections 122 are cut-away from the interior of the body 122. Grooved sections 122 may have a variety of depths and widths depending on the application. In one embodiment, grooved sections have the same width as the channel 120.

In one embodiment as illustrated in FIG. 5, apertures 125 are positioned on the body 112. Apertures 125 may be positioned at a variety of locations on the body 112. In one embodiment, apertures 125 are spaced on each side of one of the channels 120. The apertures 125 capture the interbody trial head 152, creating a temporary lock connection to the interbody trial 150. In one embodiment, a slot 127 having a narrow width and elongated length extends along the body 112. Slot 127 may have a variety of sizes and orientations. In the embodiment illustrated in FIG. 5, slot 127 is positioned between a lower edge of one channel 120 and the distal edge of the body 112, and has a length exceeding the channel 120.

Figure 6:
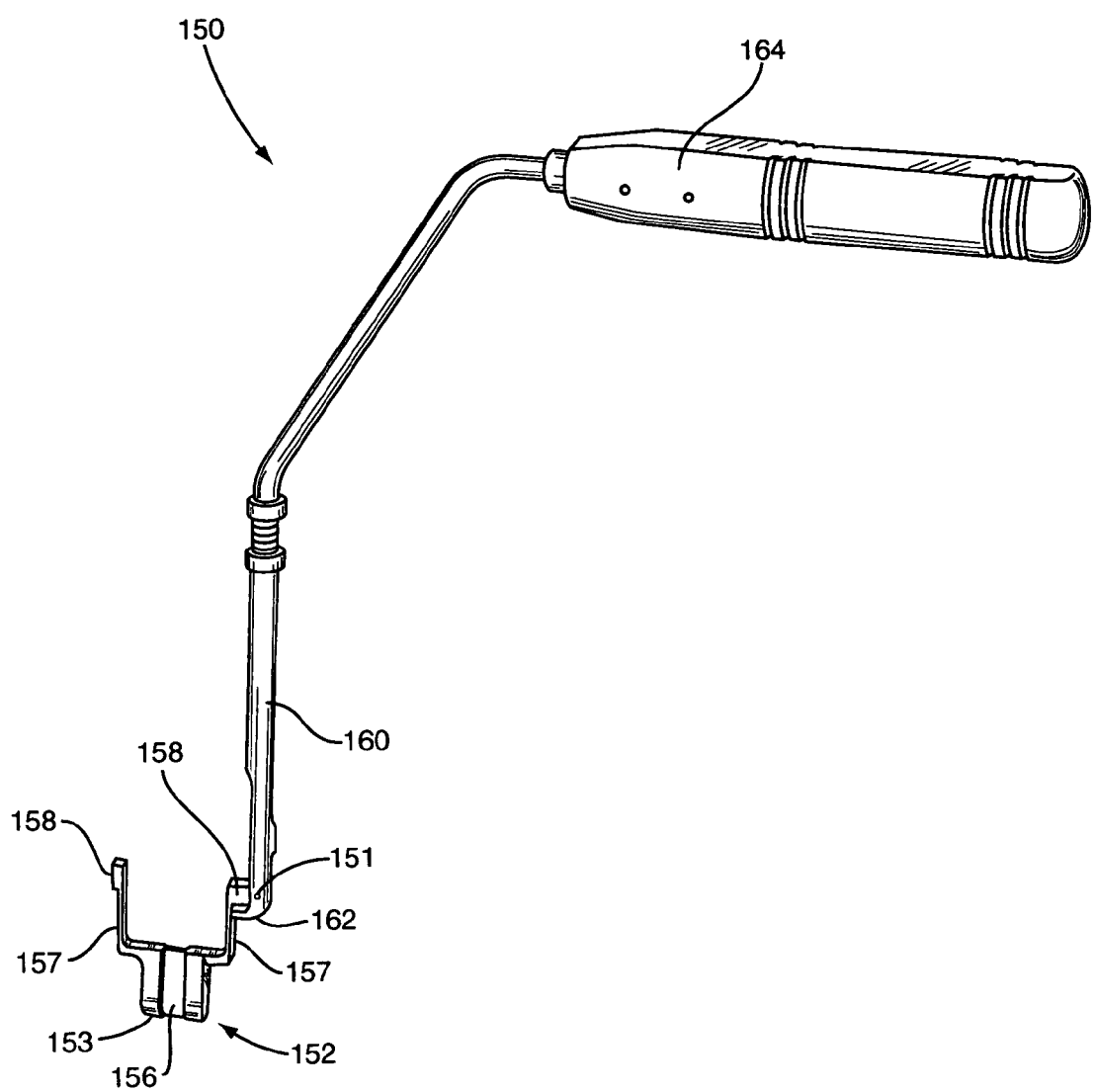
FIG. 6 is a perspective view of one embodiment of an interbody trial constructed according to the present invention.

Another foundation device 100 is an interbody trial 150 that mounts to the docking ring 110. FIG. 6 illustrates one embodiment of the interbody trial 150 having a head 152 sized to be inserted between the vertebral members 300. Head 152 has a width Q (see FIG. 7) sized to fit between the vertebral members 300 without causing distraction. In one embodiment, head 152 has a tapered configuration terminating at a tip 153. In one embodiment, indents 156 are positioned on opposing first and second sides of the head 152. The width of the head 152 is smaller at the location of the indents 156 than in the non-indented sections. In one embodiment, indents 156 are centered along the length of the head 152. Indents may have a variety of widths and depths.

Wings 157 extend from the head 152 and have a size corresponding to the grooved sections 122 of the docking ring 110. In one embodiment, wings 157 are positioned at a lateral end of the head 152 and extend outward from opposite sides. Tabs 158 extend outward from the wings 157 and may have a variety of shapes and sizes. In one embodiment, tabs 158 are positioned at the distant ends of the wings 158 and have a width greater than the width of the wings 157. In one embodiment, tabs 158 are sized to extend into the channels 120 and wings 157 sized to fit within the grooved sections 122.

A shaft 160 is connected to the head 152 and includes a locking mechanism 170 for locking the interbody trial 150 to the docking ring 110. In one embodiment, pivot 151 extends through the tab 158. The shaft 160 is adjustable between an unlocked orientation in which the shaft 160 pivots relative to the head 152, and a locked position in which the shaft 160 is fixed relative to the head 152. An extension 162 extends outward from the shaft 160 at a point distal to the pivot 151. Shaft 160 may have a variety of lengths and shapes. In one embodiment, a handle 164 provides a gripping surface.

Figure 7:
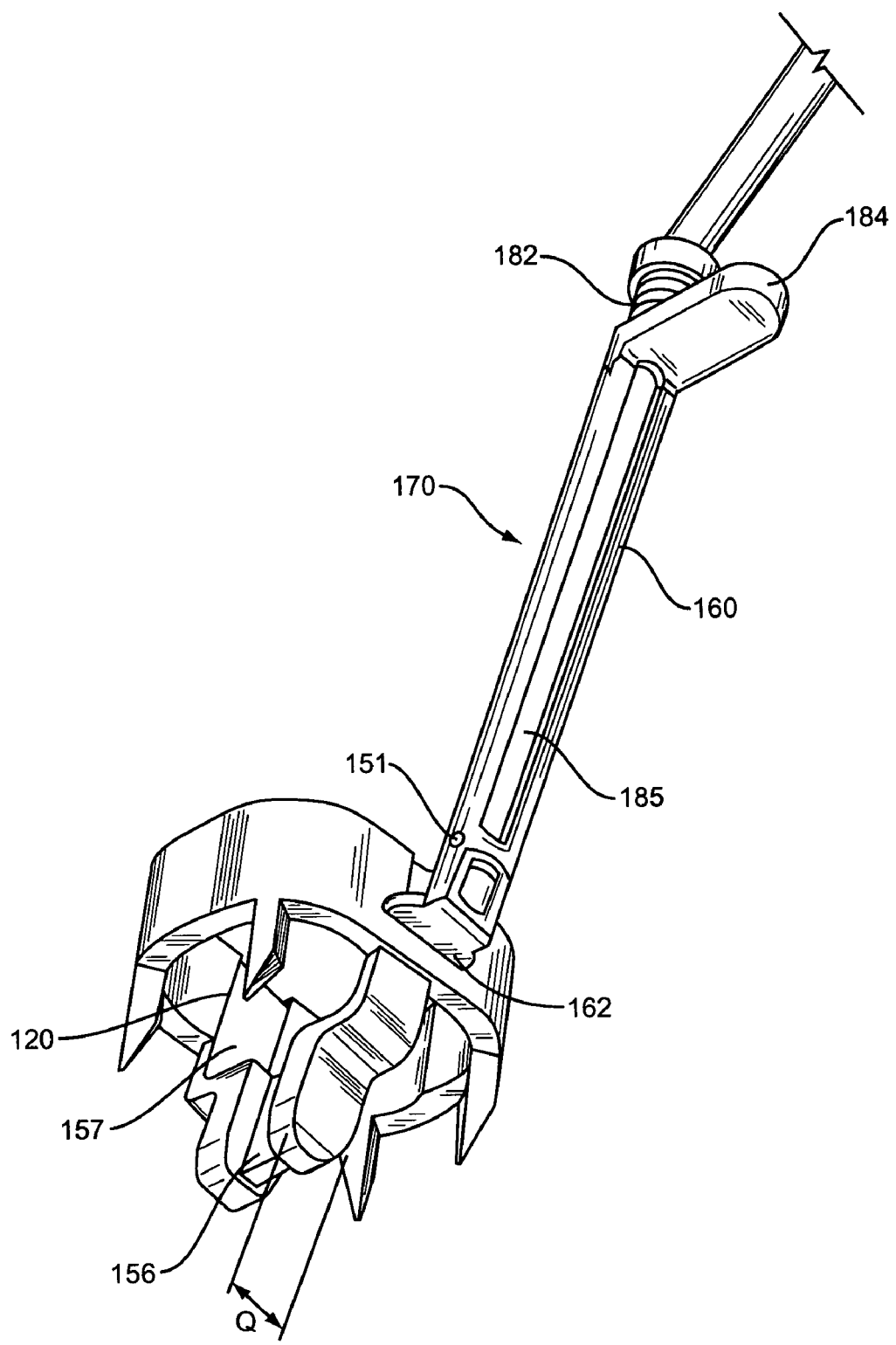
FIG. 7 is a partial perspective view of one embodiment of the docking ring attached to the interbody trial constructed according to the present invention.

FIG. 7 illustrates one embodiment of the interbody trial 150 mounted to the docking ring 110. During mounting, the wings 157 of the interbody trial 150 fit and slide within the grooved sections 122 of the docking ring 110. Complete insertion occurs when the wings 157 bottom out in the grooved sections 122 as the tabs 158 of the interbody trial 150 contact the edge of the channels 120. The shaft 160 of the interbody trial 150 is pivoted such that the extension 162 is inserted within the slot 127 of the docking ring 110. The locking mechanism 170 is then locked with the interbody trial 150 fixedly attached to the docking ring 110.

Figure 8:
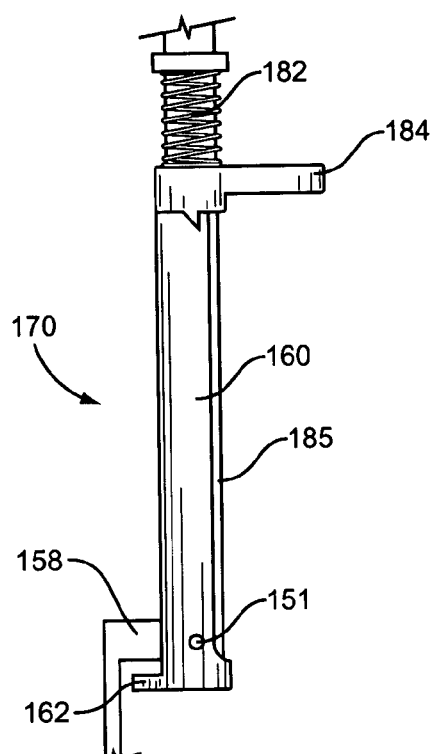
FIG. 8 is a partial side view of a locking mechanism in a locked orientation according to the present invention.
Figure 9:
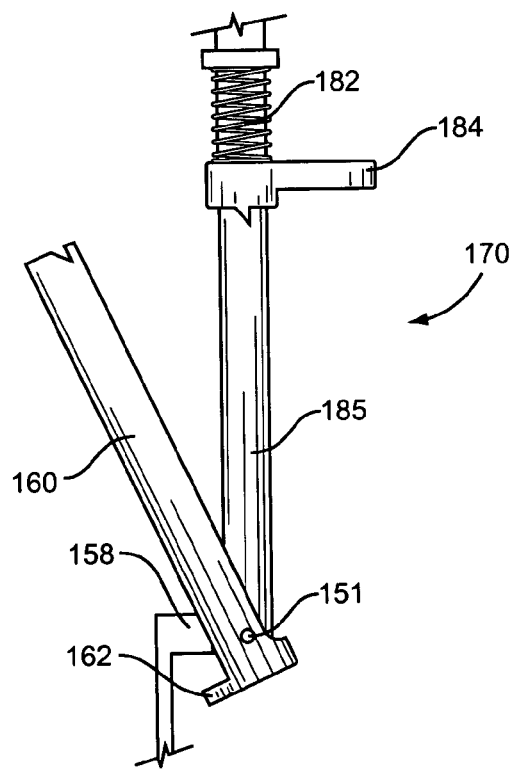
FIG. 9 is a partial side view of a locking mechanism in an unlocked orientation according to the present invention.

FIGS. 8 and 9 illustrate the locking mechanism 170. FIG. 8 illustrates the locking mechanism 170 in a locked orientation. A biasing member 182 forces an extension 184 against a proximal end of the shaft 160. Extension 184 and shaft 160 include features that mate together in the locked orientation. In this position, the extension 162 can be mounted within the slot 127 of the docking ring 110. FIG. 9 illustrates the locking mechanism 170 in an unlocked orientation. The extension 184 has been moved against the force of the biasing member 182 such that shaft 160 can move about pivot 151. Movement of the shaft 160 releases the extension 162 from the docking ring 110. In one embodiment, an inner shaft 185 is positioned within the shaft 160. Shaft 160 is movable relative to inner shaft 185 to move between the locked and unlocked orientations.

In one embodiment, docking ring 110 and interbody trial 150 are mounted together prior to attachment to the vertebral members 300. The term docking ring/trial will be used herein to define the orientation with the docking ring 110 mounted with the interbody trial 150. In one embodiment, the head 152 is positioned within the midline of the disc space 310 between the vertebral members 300.

Figure 10:
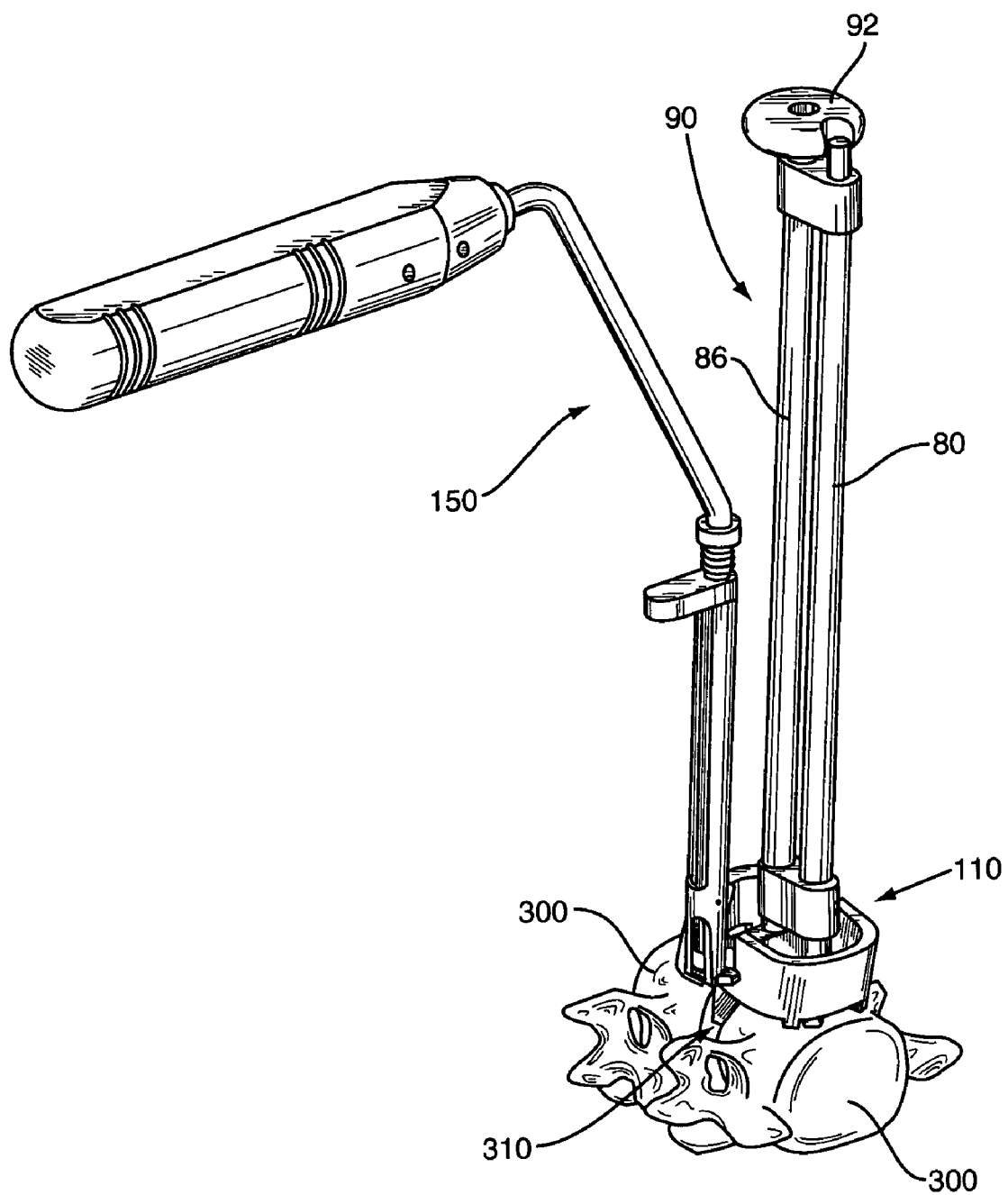
FIG. 10 is a perspective view illustrating the docking ring, interbody trial, stylus, and impactor positioned relative to the vertebral members according to the present invention.

In one embodiment, a gauge 90 is connected to the docking ring/trial to control the depth the spikes 116 are impacted into the vertebral members 300. FIG. 10 illustrates one embodiment illustrating the gauge 90 attached to the docking ring/trial. Gauge 90 includes a stylus 80 having an elongated length with a distal end that contacts the anterior face of a vertebral member 300. A second shaft 86 is in contact with the docking ring/trial. In one embodiment, second shaft 86 is mounted to the docking ring/trial. In another embodiment, second shaft 86 is positioned to contact the docking ring/trial, but is not mounted to the docking ring/trial. The proximal end of the second shaft 86 includes a head 92. In one embodiment, head 92 includes a cut-out for positioning the stylus 80. The docking ring/trial is positioned with the window 114 over the endplates of the vertebral members 300 and the disc space 310. An impacting force applied to the head 92 is distributed through the second shaft 86 and into the docking ring/trial for mounting the spikes 116 into the vertebral members 300. The depth is adjusted such that the proximal end of the stylus 80 is about flush with the head 92. In one embodiment, head 92 includes a cut-out section in which the stylus 80 is positioned. The gauge 90 is removed once the docking ring/trial has been impacted into the vertebral members 300.

Once the docking ring/trial has been mounted to the vertebral members 300, the interbody trial 150 may be detached from the docking ring 110, and reattached as needed. In one embodiment, detaching the interbody trial 150 includes unlocking the locking mechanism 170, pivoting the shaft 160 relative to the head 152, removing the interbody trial extension 162 from the docking ring slot 127, and lifting the interbody trial away from the docking ring 110. Reattaching the interbody trial 150 is accomplished in the reverse manner.

Figure 11:
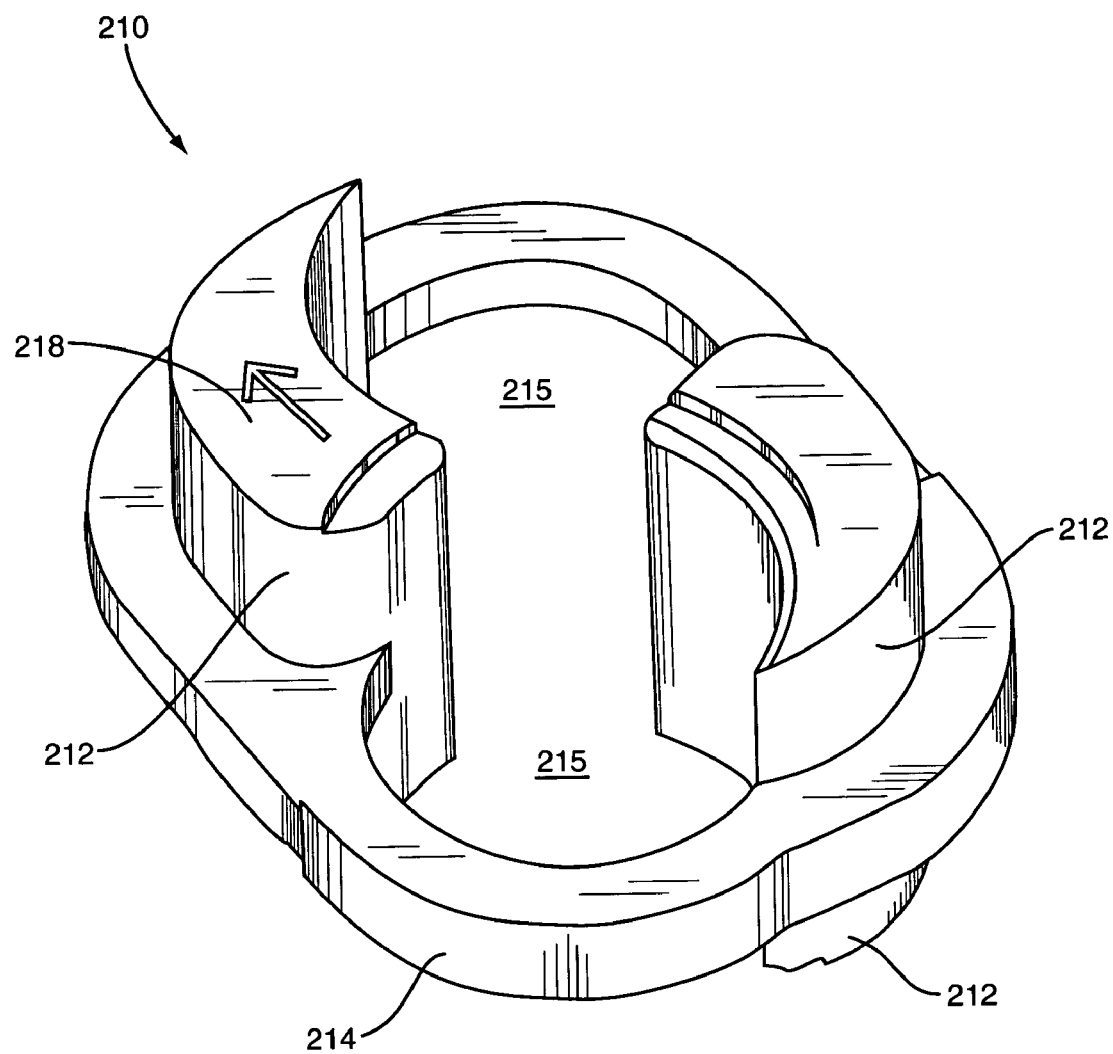
FIG. 11 is a perspective view of one embodiment of a planing guide constructed according to the present invention.

In one embodiment, it is necessary to remove the anterior surface of the vertebral members 300 so the implant 600 is positioned securely on the bone. However, not too much bone on the anterior surface should be removed because the more bone that is removed on the anterior surface, the closer the posterior end of the implant will be positioned to the spinal cord. In smaller patients, this is more critical since this distance is smaller. A planing guide 210 controls the gardening depths and areas of the vertebral members 300. One embodiment is illustrated in FIG. 11 and includes a plurality of apertures 215 formed by a flange 214 and extensions 212. The flange 214 is positioned around a portion or the entire periphery of the planing guide 210, and the extensions 212 extend outward a distance above the flange 214.

In one embodiment, the planing guide 210 includes inverting offset first and second sides. The term "inverting offset" defines the planing guide 210 is positionable in a first orientation with a first side facing upward such that apertures 215 are positioned over a first anterior section of the vertebral members 300. In a second orientation, planing guide 210 is flipped such that a second side faces upward (i.e., the first side faces downward) with the apertures positioned over a second anterior section of the vertebral members 300. The first and second anterior sections should have some area in common.

Figure 12:
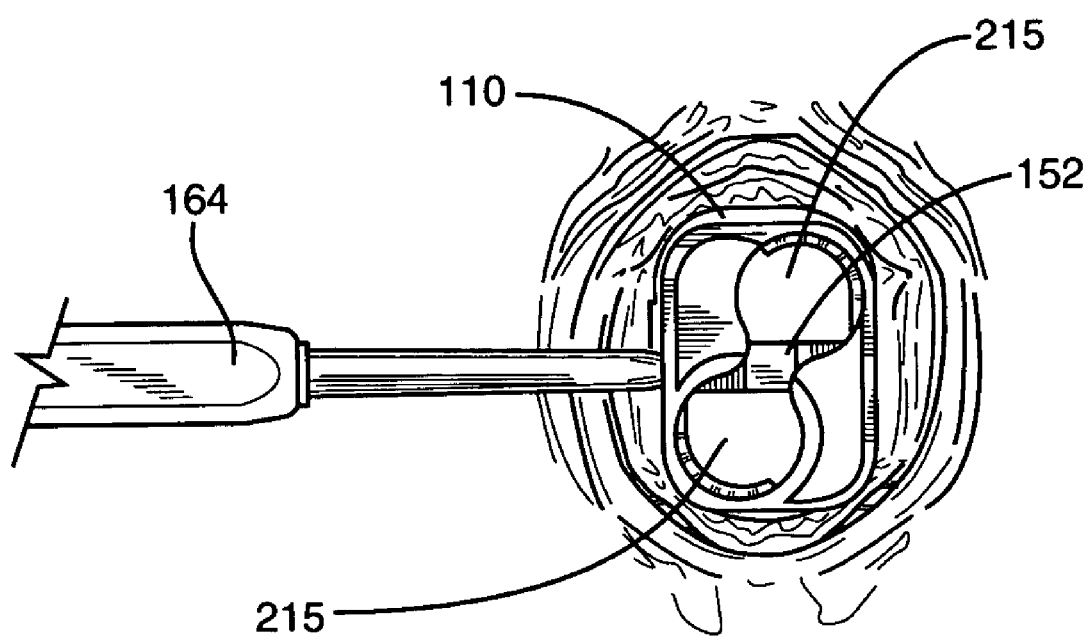
FIG. 12 is a partial front view of the planing guide mounted within the docking ring and interbody trial constructed according to the present invention.

FIG. 12 illustrates the planing guide 210 mounted within the docking ring 110. The extensions 212 fit within the body 112 and the flange 214 contacts the proximal edges of the body 112. A reamer (not illustrated) fits within the apertures 215 to garden the exposed anterior surfaces of the vertebral members 300. Once complete, the planing guide 210 is inverted (i.e., the first side which previous faced upward now faces downward towards the vertebral members 300) to garden the anterior surface accessible through the apertures 215. In the embodiment illustrated in FIG. 12, the interbody trial 150 remains attached to the docking ring 110 during the gardening process. In one embodiment, an indicator 218 is positioned on the first and second sides indicating the proper alignment of the planing guide 210. In one embodiment, the indicator 218 is an arrow. In one embodiment, the planing guide 210 is correctly positioned when the indicator points cephalad.

Figure 13:
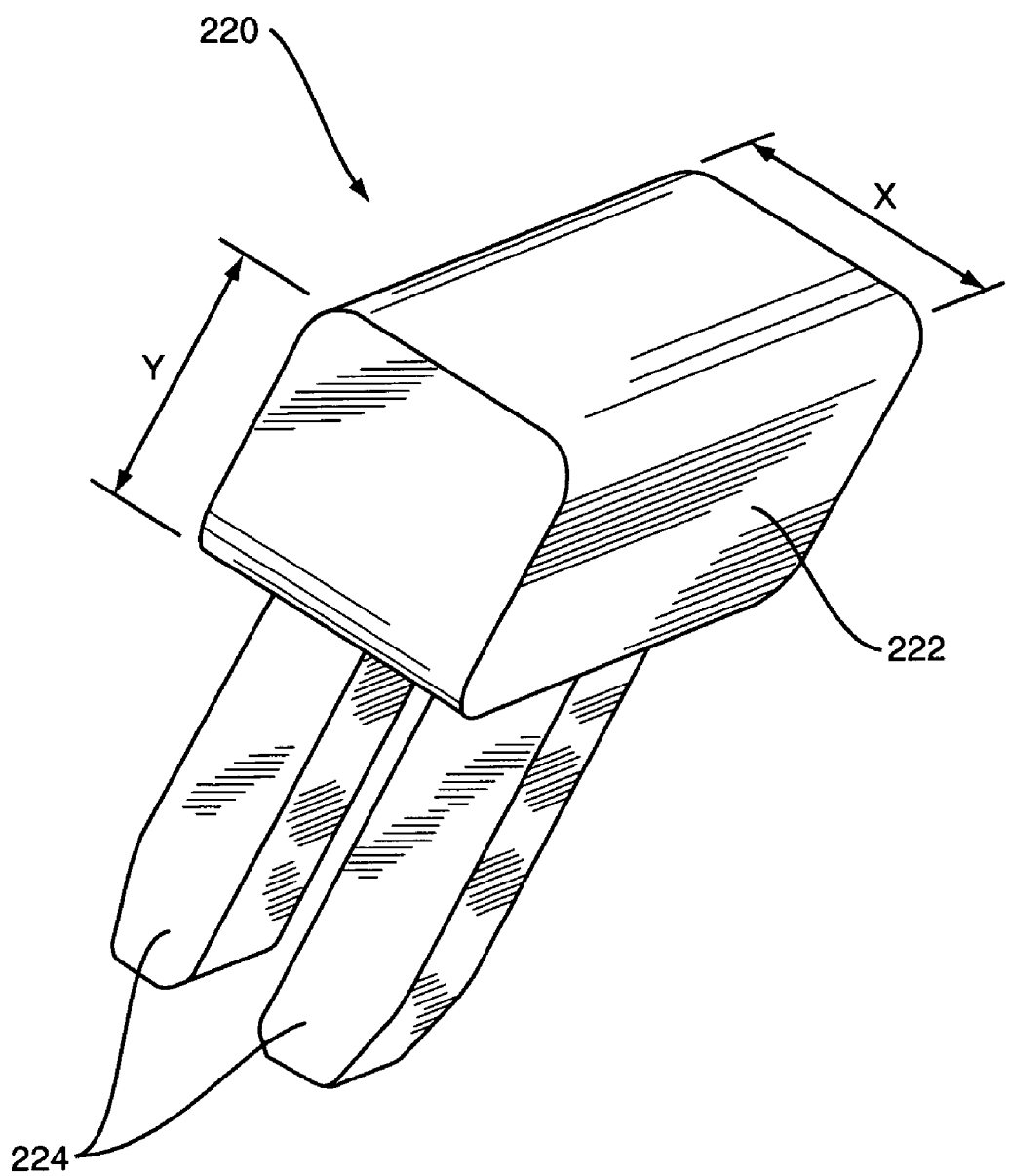
FIG. 13 is a perspective view of one embodiment of a saw guide constructed according to the present invention.

In one embodiment, a saw guide 220 is attached to the docking ring/trial to control the saw blade 230. One embodiment is illustrated in FIG. 13 and includes a body 222 having a width x and a height y. In one embodiment, width x is about equal to the normal disc height. Fingers 224 extend outward from the body 222 and are spaced a distance apart to mount to the indents 156. When fully seated, the underside of the body 222 contacts the upper side of the head 152 with the fingers 224 straddling the head 152. The body width x controls the amount of bone removed from the endplates of the vertebral members 300. The body depth y controls the depth that the bone is removed posteriorly from the vertebral members 300.

Figure 14:
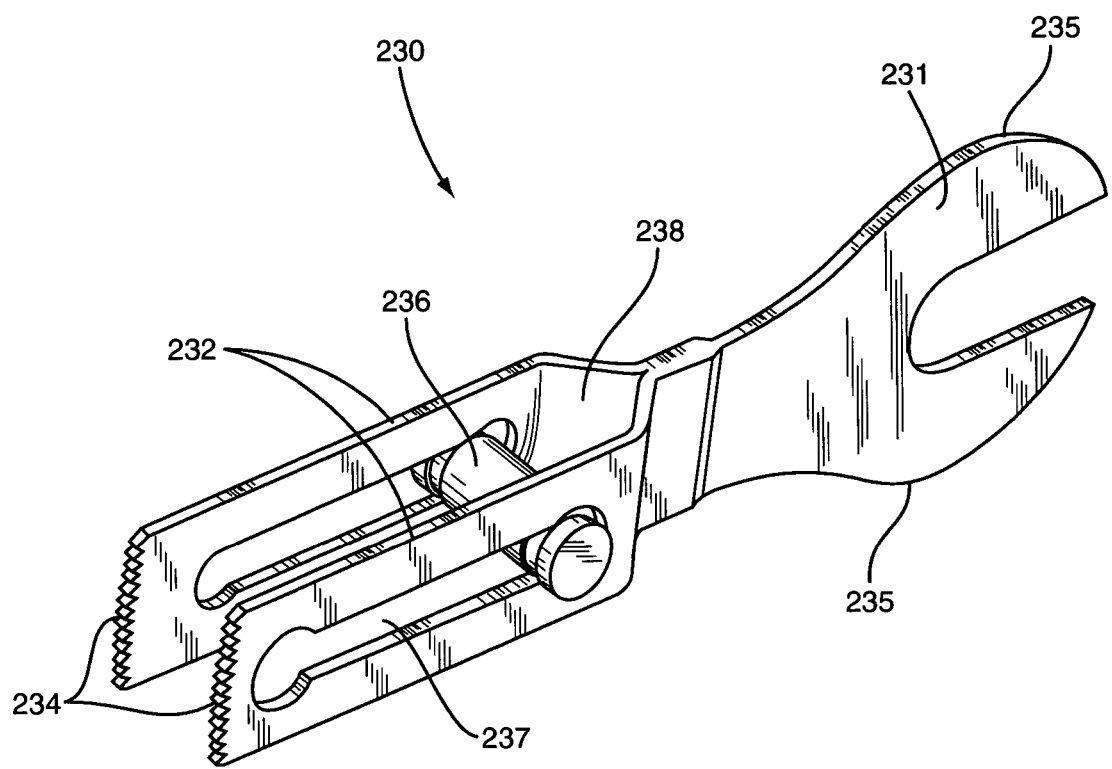
FIG. 14 is a perspective view of one embodiment of a saw blade constructed according to the present invention.
Figure 15:
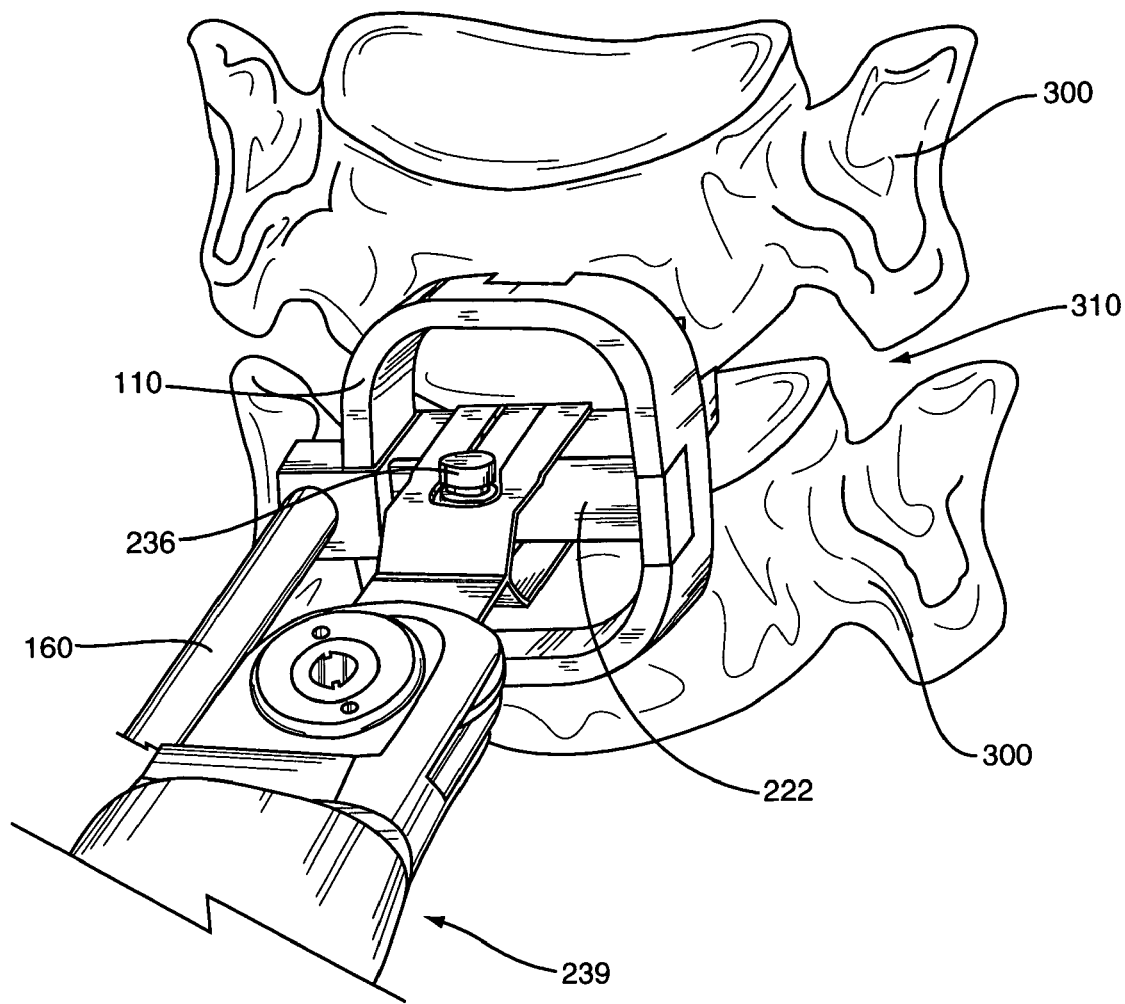
FIG. 15 is a partial perspective view of the saw blade, saw guide, interbody trial, and docking ring constructed according to one embodiment of the present invention.

A saw blade 230 removes bone from the vertebral members 300. One embodiment of the saw blade is illustrated in FIG. 14 and includes a pair of arms 232 separated by a predetermined distance. The arms 232 are separated to straddle the saw guide 220 with a first arm on a first side of the body 222 and a second arm on the second side of the body 222. Cutting surfaces 234 are positioned at the distal ends of each arm for simultaneously cutting the first and second vertebral members 300. In one embodiment, cutting surfaces 234 are parallel to cut the vertebral members 300 in a parallel manner to receive the implant 600. In one embodiment, a pin 236 extends between slots 237 within each arm 232. Pin 236 serves as a depth gauge and contacts the proximal edge of the saw guide body 222 up full insertion. In another embodiment, a forked section 238 between the arms 232 acts as a depth gauge. In one embodiment, the distance between the cutting edge and the depth gauge (either the pin 236 or forked section) is equal to the height y plus the length of the fingers 224 to control the maximum depth of cutting and prevent cutting into the spinal cord. An attachment 231 positioned on a proximal end of the saw blade 230 provides for attachment to a power source 239.

Edges 235 mate with a rail guide 221 to position the saw blade 230 at the correct angle as explained below.

FIG. 14 illustrates one embodiment of the saw blade 230 cutting the vertebral members 300. Saw blade 230 straddles the saw guide body 222 and pin 236 controls the depth of the cutting. In one embodiment, saw blade 230 has a width less than the width of the docking ring 110. A series of up-and-down passes at different lateral positions is required to cut the complete width of the vertebral members 300. By way of example, a first cut is made at a left section of the vertebral members 300, a second cut at a central section, and a third cut at a right section. Each cut is aligned with the previous cut or overlaps the previous cut resulting in a complete cut of the vertebral members 300. In one embodiment, the cutting surface 234 has a width about equal to the width of the desired cut. In this embodiment, only a single cut is required. In one embodiment, the shaft 160 acts as a guide for aligning the power source 239 relative to the vertebral member 300. Embodiments of power sources 239 include a rechargeable battery, gas turbine mechanism, and any standard electrical source, such as 110 volt, 60 cycle power sources, with or without a transformer to reduce the voltage as necessary.

Various embodiments of the saw blade 230 are included within the present invention. In one embodiment, saw blade 230 includes a single arm 232 with a single cutting surface 234. U.S. patent application Ser. No. 10/174,923 filed Jun. 16, 2002 entitled "Guide and Blade for Contouring Vertebral Bodies" is owned by the owner of the present application and is incorporated by reference in its entirety and discloses numerous saw blade embodiments.

Figure 16:
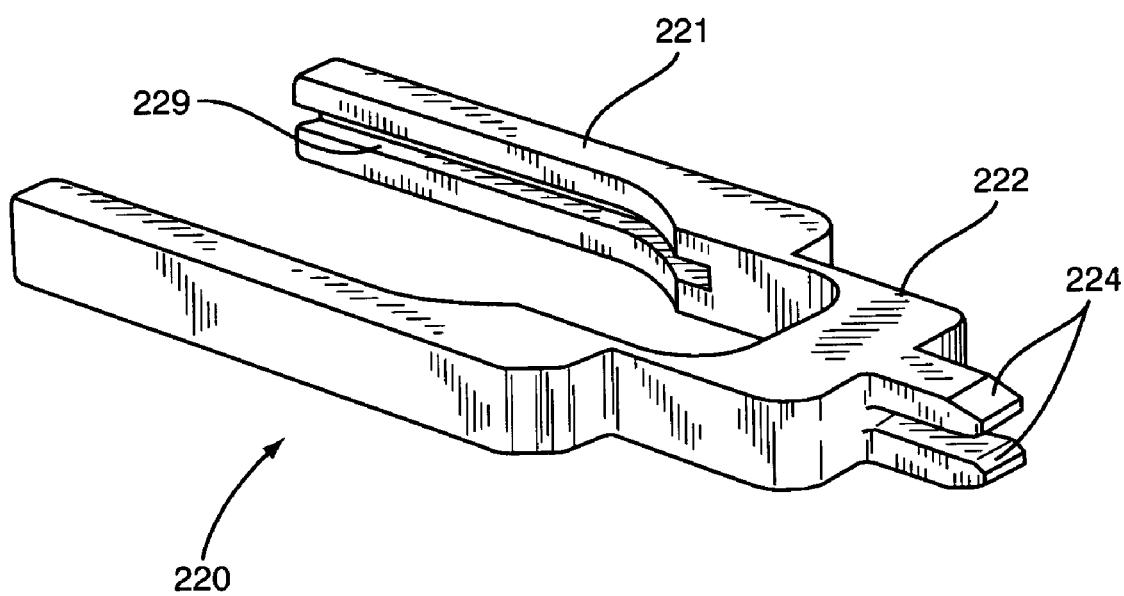
FIG. 16 is a perspective view of one embodiment of a saw guide and rail guides constructed according to the present invention.
Figure 17:
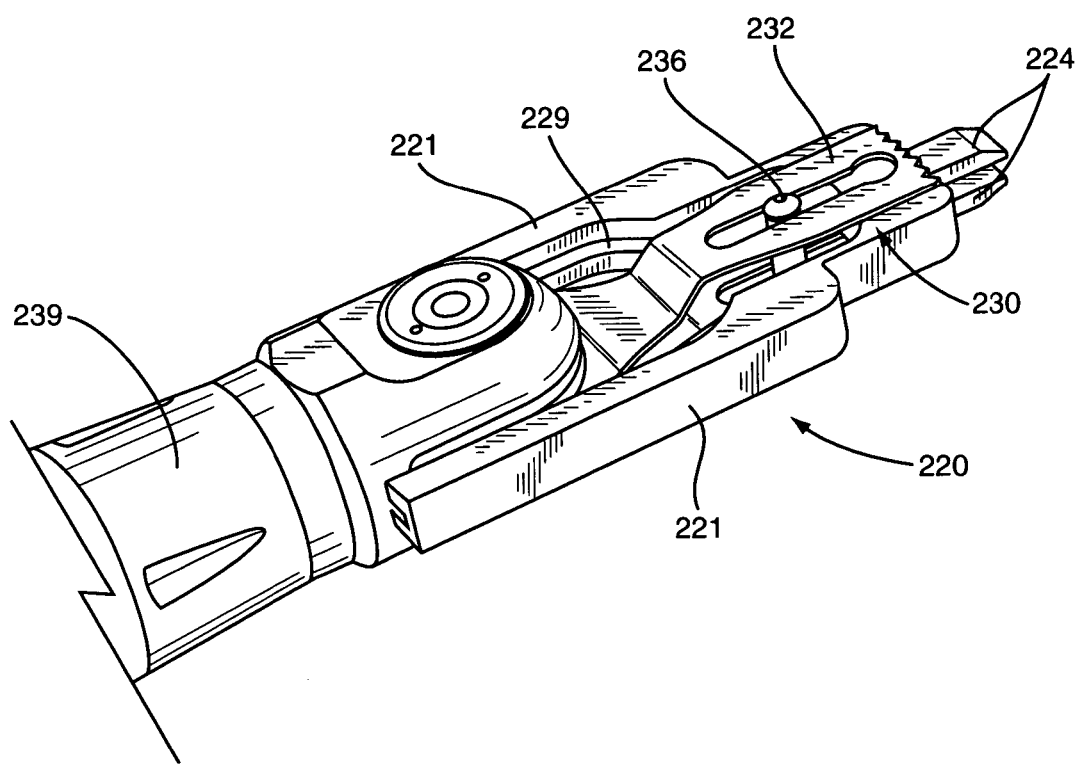
FIG. 17 is a partial perspective of one embodiment of the saw blade mounted to a power source and aligned within the rail guides according to the present invention.

Another embodiment of the saw guide 220 is illustrated in FIG. 16. Saw guide 220 includes rail guides 221 that extend from the body 222. A slot 229 within each rail guide 221 is sized for receiving the edge 235 of the saw blade 230. A proximal end of the rail guide 221 is open for receiving the saw blade 230. Slots 229 may extend the entire length of the rail guide 221, or a portion thereof. Fingers 224 mount about the interbody trial 150 to position the rail guides 221 at the proper angle. FIG. 17 illustrates the saw blade 230 positioned within the saw guide 220. Rail guide 221 controls the angle of the saw blade 230 to ensure the vertebral members 300 are cut at the proper angle.

Figure 18:
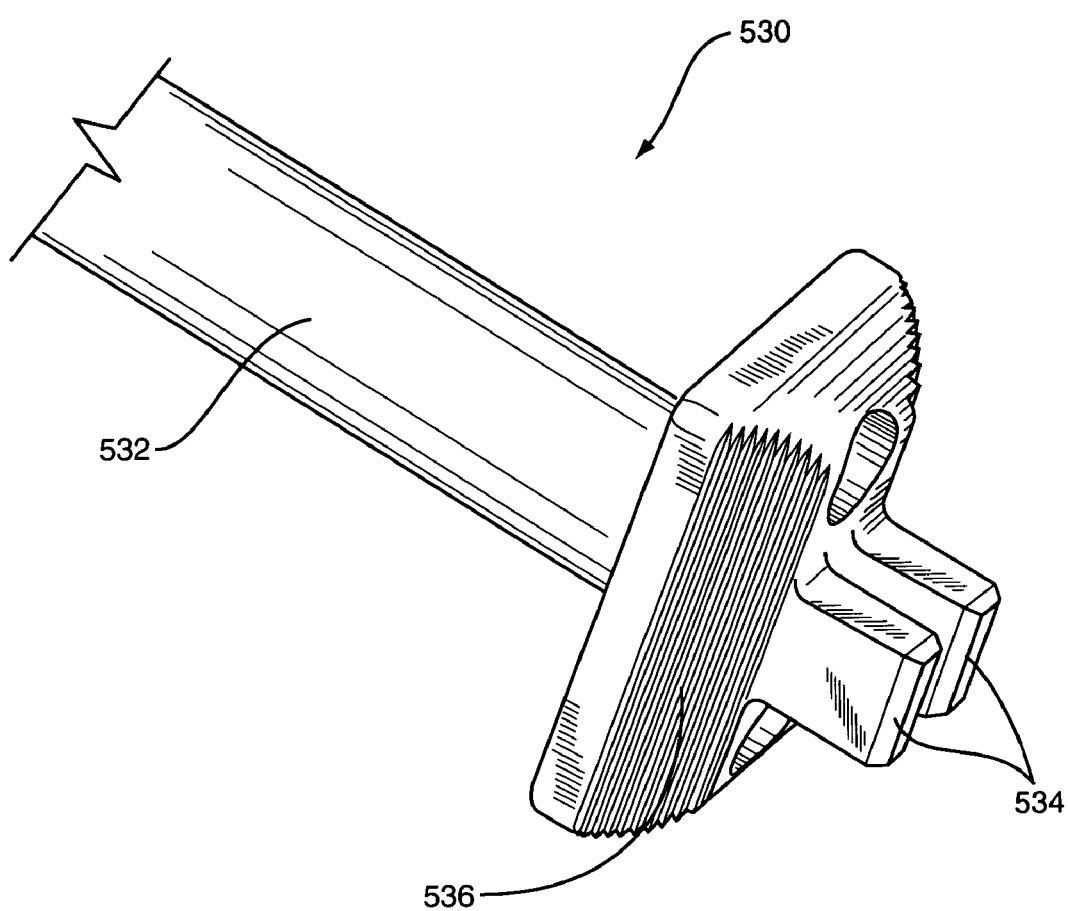
FIG. 18 is a partial perspective view of one embodiment of a chamfer tool constructed according to the present invention.
Figure 19:
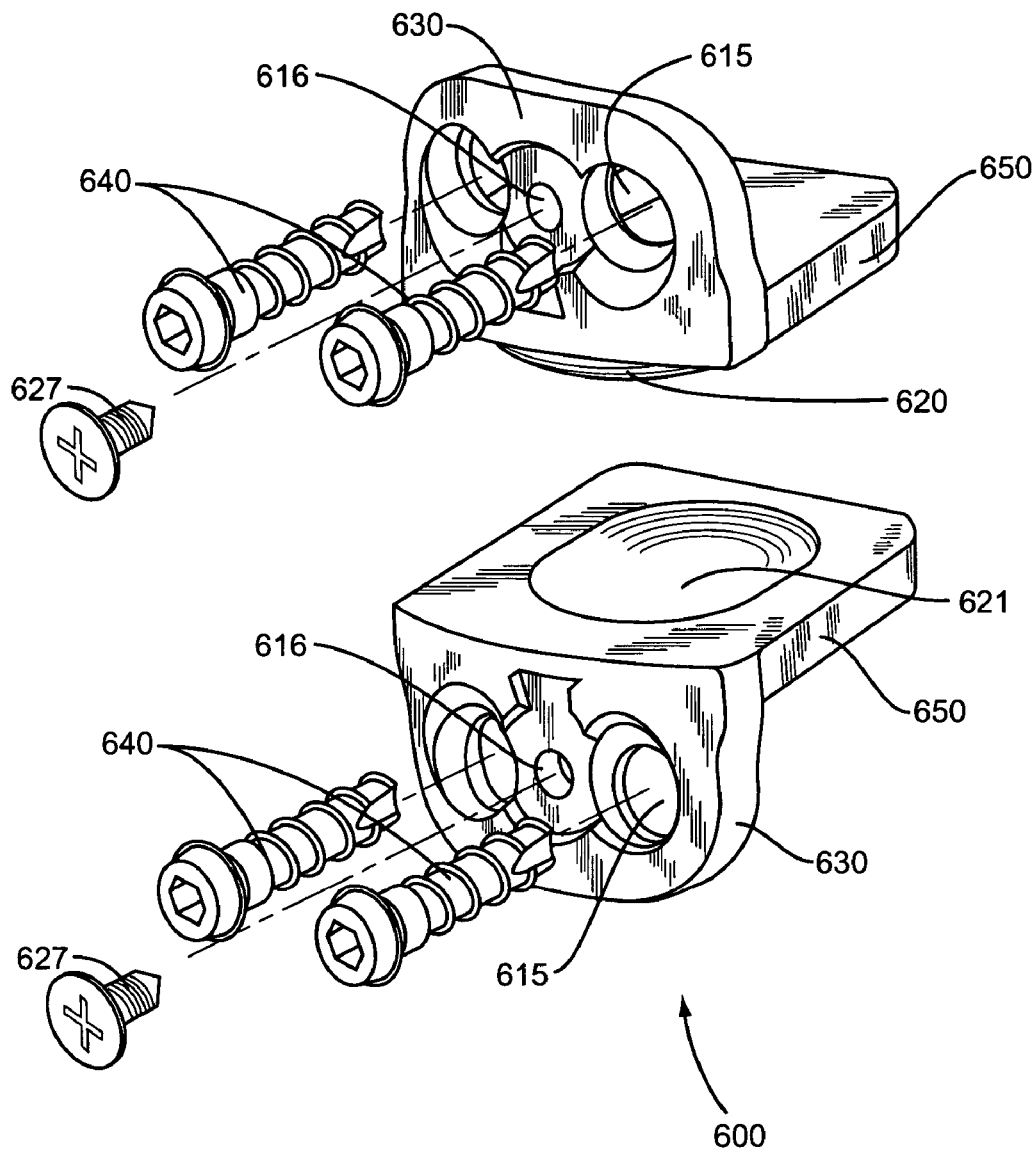
FIG. 19 is an exploded perspective view of one embodiment of an implant and fasteners constructed according to the present invention.

In one embodiment, a chamfer is created on the vertebral members 300. FIG. 18 illustrates one embodiment of the chamfer tool 530 that includes fingers 534 spaced apart to fit within the interbody trial indents 156. Teeth 536 are positioned to chamfer both the superior and inferior corners of the vertebral members 300 creating a chamfer that better matches the radius on the implant 600. A shaft 532 provides for manipulating and positioning the chamfer tool 530. After the vertebral members 300 have been prepared, the docking ring/trial is removed. Various types of implants 600 may be positioned within the disc space 310 between the vertebral members 300. In one embodiment, implant 600 is a motion-preserving device. One specific embodiment is illustrated in FIG. 19 and includes first and second members. Each member includes a mounting section 630 which mounts to an anterior surface of the vertebral member 300. One or more apertures 615 are positioned within the mounting section 630 to receive fasteners 640. In one embodiment, a locking screw and washer 627 are attached to the mounting section 630 and positioned over the heads of the fasteners 640 to prevent inadvertent removal. Intervertebral sections 650 extend outward from the mounting section 630 and into the disc space 310 between the vertebral members 300. In one embodiment, intervertebral sections 650 include a corresponding ball section 620 and trough section 621. When mounted in position on the vertebral members 300, ball section 620 mates with trough section 621 forming an articulating joint. One embodiment of the implant 600 is the PRESTIGE DISC available from Medtronic Sofamor Danek of Memphis, Tenn. Reference is further made to U.S. patent application Ser. No. 10/042,589 entitled "Artificial Disc Implant," filed Jan. 9, 2002, U.S. Provisional Application No. 60/375,354 entitled "Articular Disc Prosthesis And Method For Implanting The Same," filed Apr. 25, 2002, U.S. patent application Ser. No. 10/263,115 entitled "Modular Intervertebral Prosthesis System," filed Oct. 2, 2002, and U.S. Pat. No. 6,113,637 entitled "Artificial Intervertebral Joint Permitting Translational And Rotational Motion," all incorporated herein by reference, for additional details concerning design of an articulating joint.

Figure 20:
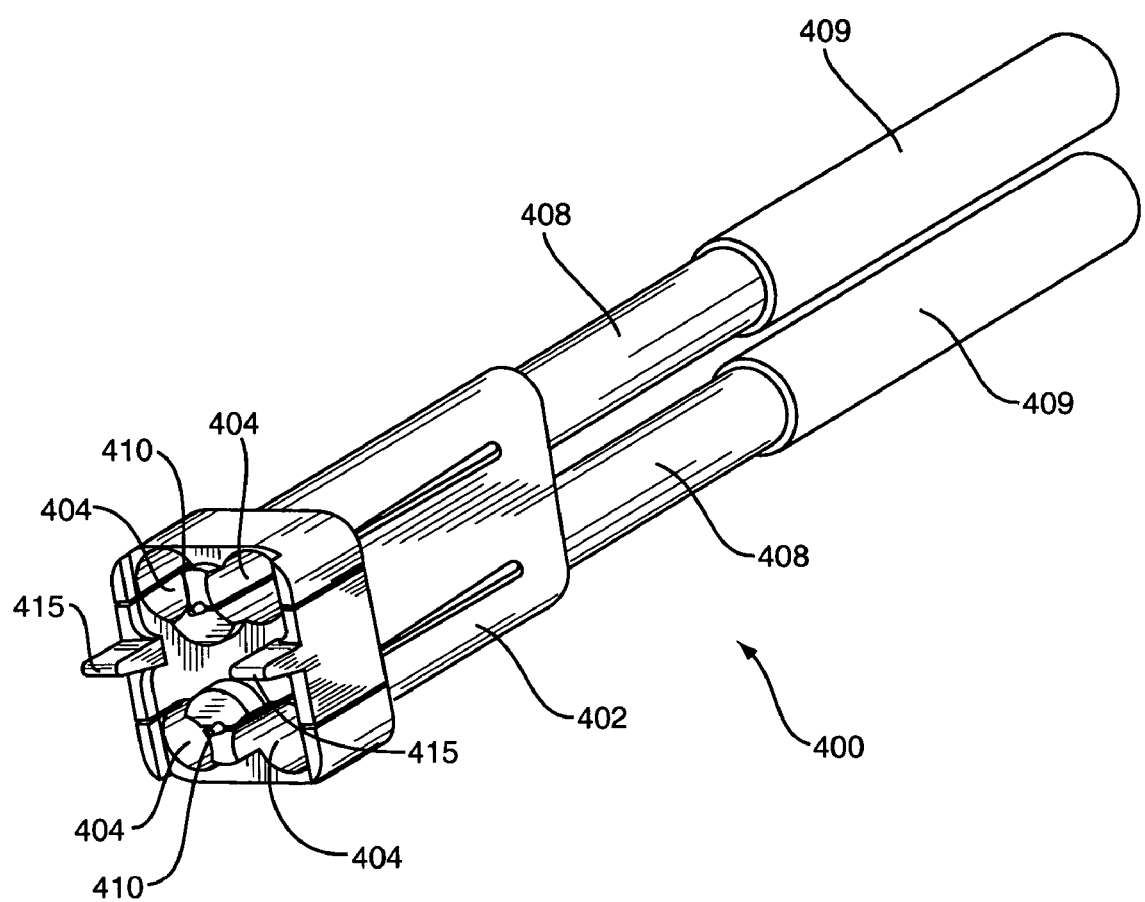
FIG. 20 is a perspective view of one embodiment of a holder constructed according to the present invention.

In one embodiment, a holder 400 holds and aligns the implant 600 relative to the vertebral members 300. FIG. 20 illustrates one embodiment having a body 402 sized to receive the implant 600. The implant mounting sections 630 abut against a distal end of the body 402 with apertures 404 aligning with apertures 615. Pins 408 include a proximal end having a handle 409 and a distal end being tapered to a point 410. Pins are movably positioned within the body 402 and are axially-movable to adjust the degree to which the point 410 extends beyond the distal end of the body 402. In one embodiment, an exterior surface of the pin 408 has helical grooves that mate with corresponding grooves within the interior of the body 402. Rotation of the pin 408 causes axial movement to adjust the position of the point 410. In one embodiment, aperture 616 in the implant mounting section 630 aligns with the point 410. One or more tangs 415 extend outward from the distal end of the body 402. In one embodiment, tangs 415 are positioned about the mid-point of the body 402.

Figure 21:
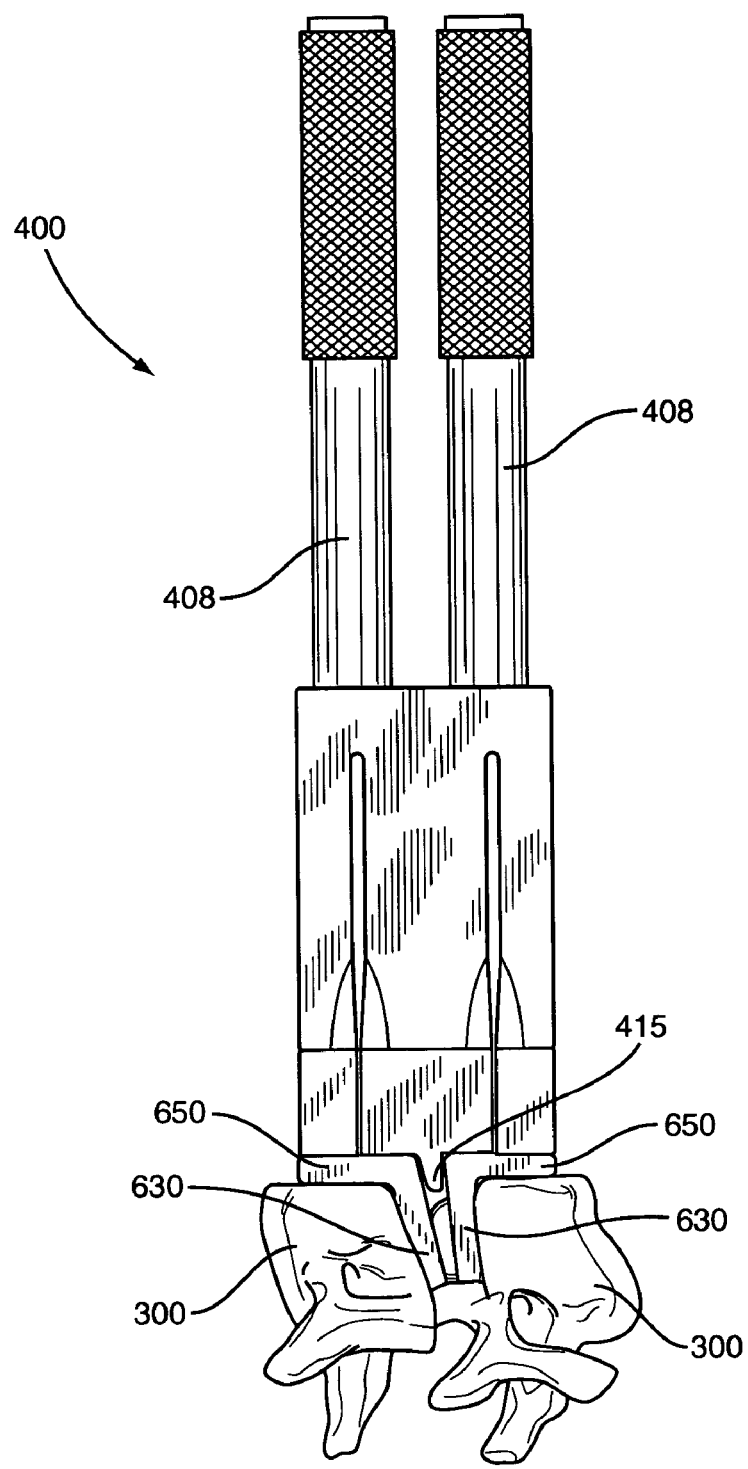
FIG. 21 is a side view of one embodiment of the holder positioning the implant between the vertebral members according to the present invention.

FIG. 21 illustrates the holder 400 and implant 600 positioned relative to the vertebral members 300. In use, the implant 600 is positioned with the mounting section 630 abutting against the distal end of the body 402 with apertures 615 aligning with apertures 404. Additionally, point 410 is aligned with the aperture 616. Tangs 415 separate the first and second implant members. In one embodiment, the pins 408 are axially moved such that points 410 extend through apertures 616 and attach the implant members to the holder 400. The holder 400 is manipulated to position the implant 600 between the vertebral members 300. A drill is used for drilling bone screw holes into the vertebral members 300. In one embodiment, a 13mm drill is used. Body 402 acts as a guide for positioning the drill at the correct angle and locating the holes at the proper position. Once the holes are drilled, fasteners 640 are inserted and tightened into position for fixedly mounting the implant 600. Pins 408 are axially moved such that the points 410 exit the vertebral members 300 and the holder 400 is removed. In one embodiment, it may be necessary to tilt the holder 400 cephalad/caudal during removal. The locking screws 627 and washers 637 are then mounted to lock the fasteners 640 in position.

Figure 22:
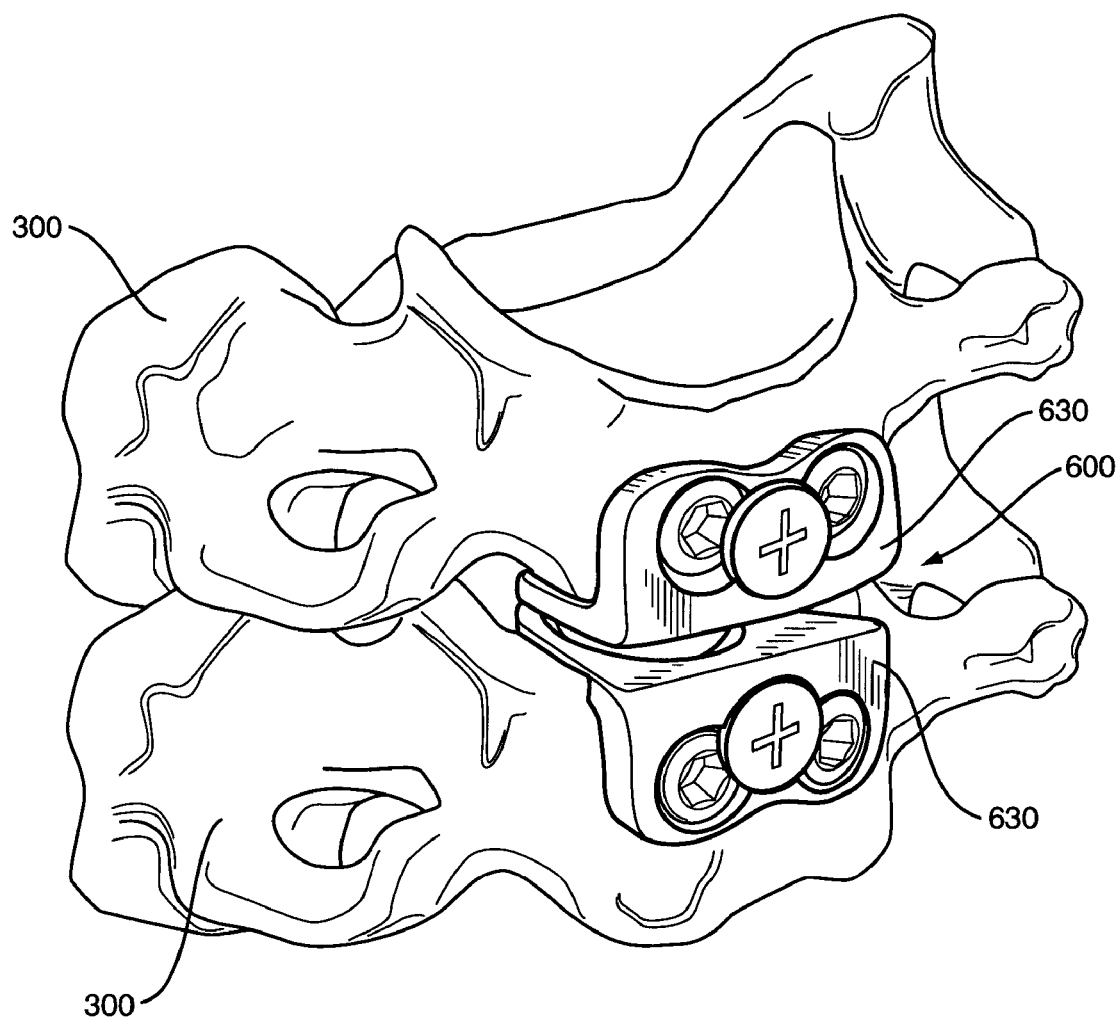
FIG. 22 is a partial perspective view of one embodiment of the implant mounted between adjacent vertebral members according to the present invention.

FIG. 22 illustrates one embodiment with the implant 600 mounted within the vertebral members 300. In this embodiment, mounting sections 630 are positioned on the anterior surface of the vertebral members 300.

Figure 23:
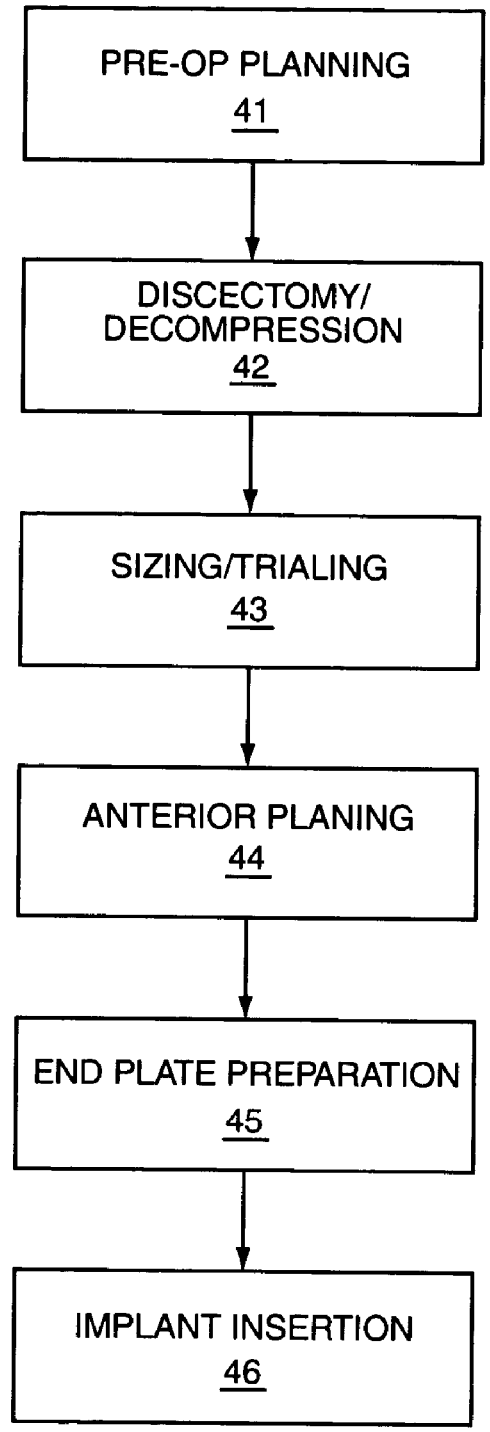
FIG. 23 is a schematic illustration of one embodiment of the steps of preparing the vertebral members and mounting an implant according to the present invention.

FIG. 23 comprises one embodiment of the steps for preparing the vertebral members 300 and inserting the implant 600. Prior to beginning the surgical procedure (step 41), the normal disc height between the vertebral members is determined. Normal disc height is defined as the distance between endplates, prior to disc disease. In one embodiment, an x-ray template is used to determine the normal disc height. In another embodiment in which either the disc space 310 or the vertebral members 300 are damaged, an adjacent disc space and/or adjacent vertebral members are sized and used as a guide for determining the normal disc height. Once the normal disc height is determined, an implant 600 is selected that is anatomically appropriately sized. In one embodiment, the implant 600 is x-rayed to determine the size. Additionally, the docking ring 110 and template trial 150 are selected to ensure compatibility with the patient's anatomy. In one embodiment, the size of the docking ring 110 is sized to ensure the spikes 116 are spaced a distance apart to mount with the first and second vertebral members 300. If the inferior or superior spikes encroach the disc space 310, or disc space of adjacent vertebral members, the docking ring 110 is not properly sized. The template trial 150 is sized to determine the width Q properly fits between the vertebral members 300 without causing distraction beyond the normal disc space.

The next step comprises discectomy and decompression (step 42). In one embodiment, fluoroscopy is used throughout the procedure. The patient is aligned with the neck in a neutral position that brings the disc space 310 to the amount of the normal disc space without over-extension. An incision is made to access the vertebral members 300. In one embodiment, the incision is a minimum of 55 mm. In one embodiment, a Smith-Robinson decompression technique is used.

Sizing and trialing (step 43) uses a template trial 510 having a width w that does not cause distraction beyond the normal disc height. A template is cut, and a high-speed burr is used to remove the templated bone both laterally and posteriorly. The docking ring 110 is then mounted to the vertebral members 300. In one embodiment, the interbody trial 150 is attached to the docking ring 110 prior to the docking ring 110 being attached to the vertebral members 300.

Anterior planing (step 44) mounts the planing guide 210 into the docking ring 110 and uses a planer to remove the bone. In one embodiment having a planing guide 210 with two openings 215, the first anterior section is planed, the planing guide 210 is inverted, and the second complementing anterior section is planed.

Endplate preparation (step 45) uses a saw guide 220 and a saw blade 230. A chamfer tool 530 may further be used to chamfer the vertebral members 300. After end plate preparation, the docking ring 110 and interbody trial 150 are removed from the vertebral members 300. In one embodiment, a slap hammer is used for removal. Any bone fragments left from the saw blade 230 or chamfer tool 530 are removed with a burr as well as any obvious obtrusions that may interfere with placement of the implant 600.

Implant insertion (step 46) is performed using the holder 400 to grasp and position the implant 600. Once positioned, the implant 600 is attached to the vertebral members 300. In one embodiment, implant 600 is inserted without the use of a holder 400. In one embodiment, implant 600 is a motion preserving implant inserted between the vertebral members 300. The combined disc height of the implant is about equal to the normal disc height.

As used herein, the term "distraction" is defined as extending the disc space between the adjacent vertebral members 300 beyond an amount of the normal disc space.

The present invention is used for contouring and shaping vertebral members within the cervical, thoracic, and lumbar regions of the spine. In one embodiment, the present invention is used for shaping and contouring the anterior sections of vertebral members. In another embodiment, the invention is used for shaping and contouring posterior sections of vertebral members. In another embodiment, the invention is used for contouring lateral sections of the vertebral members. The term vertebral member 300 is used generally to describe the vertebral geometry comprising the vertebral body, pedicles, lamina, and processes.

In one embodiment, the head 152 is used as a saw guide as the opposing first and second sides of the head control the amount of bone removed from the vertebral members 300. Head 152 further has a height to control the depth that is cut from the vertebral members 300.

The present invention may be carried out in other specific ways than those herein set forth without departing from the scope and essential characteristics of the invention. In one embodiment, the process of contouring the vertebral members comprises using a plurality of different blades 20 each having increasingly longer lengths. The present embodiments are, therefore, to be considered in all respects as illustrative and not restrictive, and all changes coming within the meaning and equivalency range of the appended claims are intended to be embraced therein.

What is claimed is:

1. A system to prepare vertebral members for an implant comprising:
   a docking ring forming a window sized to extend over a portion of the vertebral members and a disc space therebetween, the docking ring having a distal side with a plurality of spikes extending outward therefrom to extend within the vertebral members;
   a mount sized to attach to the docking ring and extend across the window, the mount comprising a receiving section and a second section, the receiving section having a first width different than a width of the second section, the mount extending below the distal side of the docking ring;
   a plurality of instruments each having a pair of fingers spaced a distance apart to mate with the receiving section and align with the vertebral members; and
   a locking mechanism mounted within the mount and having a biasing mechanism that is selectively positionable between a first orientation in which the mount is fixedly attached to the docking ring and a second orientation in which the mount can be removed from the docking ring.

2. The system of claim 1, wherein the docking ring includes a proximal side with a pair of channels positioned on opposite sides of the window and align with the disc space.

3. The system of claim 2, wherein the mount includes a pair of outwardly extending wings sized to mount within the pair of channels.

4. The system of claim 1, wherein the window has a substantially rectangular shape.

5. The system of claim 1, wherein each of said plurality of spikes has an inwardly tapering configuration to prevent splaying when mounted within the vertebral members.

6. The system of claim 1, wherein the mount is positioned along a center line of the window.

7. A device to prepare first and second vertebral members comprising:
   a ring having an outer wall forming a window, the ring having a first edge having a plurality of spikes extending outward to mount within the first and second vertebral members and receiving sections on a second edge and aligned on opposite sides of the window, wherein the receiving sections comprise channels that extend inward from the second edge and grooves that align with the channels, the receiving sections having a reduced width in the channels relative to the ring; and a trial having a head sized to extend across the window and wings extending outward a distance above the head to mount within the receiving sections;

the trial mountable with the ring with the wings positioned in the receiving sections and the head aligned across a central portion of the window and below the first edge.

8. The device of claim 7, wherein the head and the first edge are substantially parallel when the trial is mounted within the ring.

9. The device of claim 7, wherein the wings further include outwardly extending tabs positioned at a proximal end of the wings, the tabs being sized to seat within the channels and the wings seat within the grooves when the trial is mounted within the ring.

10. The device of claim 7, further comprising a shaft pivotally connected to the head and a locking mechanism comprising a spring positioned within the shaft, the locking mechanism positionable between a locked orientation with a distal end of the shaft connected to the ring, and an unlocked orientation in which the distal end is distant from the ring.

* * * * *